US010557825B2

(12) United States Patent
Safai et al.

(10) Patent No.: US 10,557,825 B2
(45) Date of Patent: Feb. 11, 2020

(54) APPARATUS, CONTROLLER, AND METHOD FOR INSPECTING A PART

(71) Applicant: The Boeing Company, Chicago, IL (US)

(72) Inventors: Morteza Safai, Newcastle, WA (US); Keith D. Humfeld, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 353 days.

(21) Appl. No.: 15/415,492

(22) Filed: Jan. 25, 2017

(65) Prior Publication Data

US 2018/0209938 A1 Jul. 26, 2018

(51) Int. Cl.
*G01N 27/90* (2006.01)
*G01N 27/82* (2006.01)

(52) U.S. Cl.
CPC ......... *G01N 27/9046* (2013.01); *G01N 27/82* (2013.01); *G01N 27/90* (2013.01)

(58) Field of Classification Search
CPC .......... G01N 27/9046; G01N 27/9006; G01N 27/9033; G01N 27/87; G01N 27/90; G01N 27/82
See application file for complete search history.

(56) References Cited

U.S. PATENT DOCUMENTS

| 5,537,037 A | 7/1996 | Otaka et al. |
| 7,304,474 B2 | 12/2007 | Rempt |
| 7,902,819 B2 | 3/2011 | Hohman et al. |
| 8,841,904 B1 | 9/2014 | Brady et al. |
| 8,947,079 B2 | 2/2015 | Yamamoto |
| 2015/0145509 A1* | 5/2015 | Takenaka ........... G01N 27/9046 324/207.21 |

OTHER PUBLICATIONS

Eddy Current Inspection: Sliding Probes, Quality Magazine, Jul. 12, 2011, pp. 1-6, http://www.qualitymag.com/articles/90089-eddy-current-inspection-sliding-probes accessed Jan. 27, 2017.

* cited by examiner

*Primary Examiner* — Amy He
(74) *Attorney, Agent, or Firm* — Kunzler Bean & Adamson

(57) ABSTRACT

Described herein is a method of inspecting a part for defects. The method includes applying an electromagnetic field to the part using a defect detection coil and one or more noise cancelation coils. The method also includes detecting feedback received in response to applying the electromagnetic field. The method includes adjusting settings corresponding to the one or more noise cancelation coils, in response to the feedback, to reduce electromagnetic noise.

17 Claims, 6 Drawing Sheets

APPARATUS, CONTROLLER, AND METHOD FOR INSPECTING A PART

FIELD

This disclosure relates generally to nondestructive testing of a part, and more particularly to inspecting a part for defects using nondestructive testing.

BACKGROUND

Eddy current testing is one electromagnetic testing method used to nondestructively detect defects in a part. In certain environments, eddy current testing uses electromagnetic induction to detect defects on a surface of a conductive material. Eddy current testing may be limited by a sensitivity of a probe used to perform the eddy current testing and/or by an edge effect. Moreover, the sensitivity of a probe may be limited by signal feedback and/or external electromagnetic noise generated by devices external to the probe. Further, the edge effect may create a non-homogeneous field that may skew a detected signal. Limited sensitivity of the probe and/or the edge effect may reduce testing sensitivity, limit an inspection area, and/or limit a depth of inspection penetration.

SUMMARY

The subject matter of the present application has been developed in response to the present state of the art, and in particular, in response to shortcomings of conventional probes used for inspection of parts for defects. For example, conventional probes do not facilitate a reduction of electromagnetic noise that may affect signals indicating defects in parts.

Accordingly, the subject matter of the present application has been developed to provide a part inspection apparatus, controller, and method that overcome at least some of the above-discussed shortcomings of prior art techniques. More particularly, in some embodiments, described herein are apparatuses, controllers, and methods for part inspection that apply an electromagnetic field to reduce electromagnetic noise.

A method of inspecting a part for defects includes applying an electromagnetic field to the part using a defect detection coil and one or more noise cancelation coils. The method also includes detecting feedback received in response to applying the electromagnetic field. The method includes adjusting settings corresponding to the one or more noise cancelation coils, in response to the feedback, to reduce electromagnetic noise. The preceding subject matter of this paragraph characterizes example 1 of the present disclosure.

The method includes determining whether the part includes a defect based on a measurement corresponding to the electromagnetic field. The preceding subject matter of this paragraph characterizes example 2 of the present disclosure, wherein example 2 also includes the subject matter according to example 1, above.

The method includes applying the electromagnetic field to the part using the defect detection coil and the one or more noise cancelation coils include applying the electromagnetic field to the part using two noise cancelation coils. The preceding subject matter of this paragraph characterizes example 3 of the present disclosure, wherein example 3 also includes the subject matter according to any one of examples 1 or 2, above.

Applying the electromagnetic field includes locating a probe in close proximity with the part and activating the probe, and the probe includes the defect detection coil and the one or more noise cancelation coils. The preceding subject matter of this paragraph characterizes example 4 of the present disclosure, wherein example 4 also includes the subject matter according to any one of examples 1, 2, or 3, above.

The defect detection coil produces a first electromagnetic field and the one or more noise cancelation coils produce a second electromagnetic field. The preceding subject matter of this paragraph characterizes example 5 of the present disclosure, wherein example 5 also includes the subject matter according to any one of examples 1, 2, 3, or 4, above.

The second electromagnetic field cancels at least a portion of the first electromagnet field to produce a low electromagnetic field at the portion of the first electromagnetic field. The preceding subject matter of this paragraph characterizes example 6 of the present disclosure, wherein example 6 also includes the subject matter according to any one of examples 1, 2, 3, 4, or 5, above.

The low electromagnetic field is a zero electromagnetic field. The preceding subject matter of this paragraph characterizes example 7 of the present disclosure, wherein example 7 also includes the subject matter according to any one of examples 1, 2, 3, 4, 5, or 6, above.

Detecting feedback received in response to applying the electromagnetic field includes receiving feedback using a feedback detection coil. The preceding subject matter of this paragraph characterizes example 8 of the present disclosure, wherein example 8 also includes the subject matter according to any one of examples 1, 2, 3, 4, 5, 6, or 7, above.

Adjusting settings corresponding to the one or more noise cancelation coils in response to the feedback includes adjusting a voltage supplied to the one or more noise cancelation coils. The preceding subject matter of this paragraph characterizes example 9 of the present disclosure, wherein example 9 also includes the subject matter according to any one of examples 1, 2, 3, 4, 5, 6, 7, or 8, above.

An apparatus for inspecting a part for defects includes a probe having a defect detection coil configured to produce a first electromagnetic field for detecting a defect in the part. The probe also includes one or more noise cancelation coils configured to produce a second electromagnetic field to cancel out at least a portion of the first electromagnetic field. The probe includes a feedback detection coil configured to detect feedback produced by the first electromagnetic field, the second electromagnetic field, or some combination thereof. The preceding subject matter of this paragraph characterizes example 10 of the present disclosure.

Settings corresponding to the one or more noise cancelation coils are adjusted in response to the feedback to reduce electromagnetic noise. The preceding subject matter of this paragraph characterizes example 11 of the present disclosure, wherein example 11 also includes the subject matter according to example 10, above.

A voltage supplied to the one or more noise cancelation coils is used to adjust the settings corresponding to the one or more noise cancelation coils. The preceding subject matter of this paragraph characterizes example 12 of the present disclosure, wherein example 12 also includes the subject matter according to any one of examples 10 or 11, above.

A measurement corresponding to the first electromagnetic field is used to determine whether the part includes a defect. The preceding subject matter of this paragraph characterizes example 13 of the present disclosure, wherein example 13 also includes the subject matter according to any one of examples 10, 11, or 12, above.

The one or more noise cancelation coils include two noise cancelation coils. The preceding subject matter of this paragraph characterizes example 14 of the present disclosure, wherein example 14 also includes the subject matter according to any one of examples 10, 11, 12, or 13, above.

A low electromagnetic field is produced at the portion of the first electromagnetic field. The preceding subject matter of this paragraph characterizes example 15 of the present disclosure, wherein example 15 also includes the subject matter according to any one of examples 10, 11, 12, 13, or 14, above.

The low electromagnetic field facilitates increasing the ability of the probe to detect a defect in the part. The preceding subject matter of this paragraph characterizes example 16 of the present disclosure, wherein example 16 also includes the subject matter according to any one of examples 10, 11, 12, 13, 14, or 15, above.

The second electromagnetic field blocks external noise from affecting detection of a defect. The preceding subject matter of this paragraph characterizes example 17 of the present disclosure, wherein example 17 also includes the subject matter according to any one of examples 10, 11, 12, 13, 14, 15, or 16, above.

A controller for controlling inspection of a part for defects includes a defect detection module that controls a defect detection coil to produce a first electromagnetic field for detecting a defect in the part. The controller also includes a noise cancelation control module that controls one or more noise cancelation coils to produce a second electromagnetic field to cancel out at least a portion of the first electromagnetic field. The controller includes a feedback module that receives feedback produced by the first electromagnetic field, the second electromagnetic field, or some combination thereof. The preceding subject matter of this paragraph characterizes example 18 of the present disclosure.

The noise cancelation control module adjusts settings corresponding to the one or more noise cancelation coils in response to the feedback to reduce electromagnetic noise. The preceding subject matter of this paragraph characterizes example 19 of the present disclosure, wherein example 19 also includes the subject matter according to example 18, above.

The defect detection module determines whether the part includes a defect based on a measurement corresponding to the first electromagnetic field. The preceding subject matter of this paragraph characterizes example 20 of the present disclosure, wherein example 20 also includes the subject matter according to any one of examples 18 or 19, above.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter, they are not therefore to be considered to be limiting of its scope. The subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
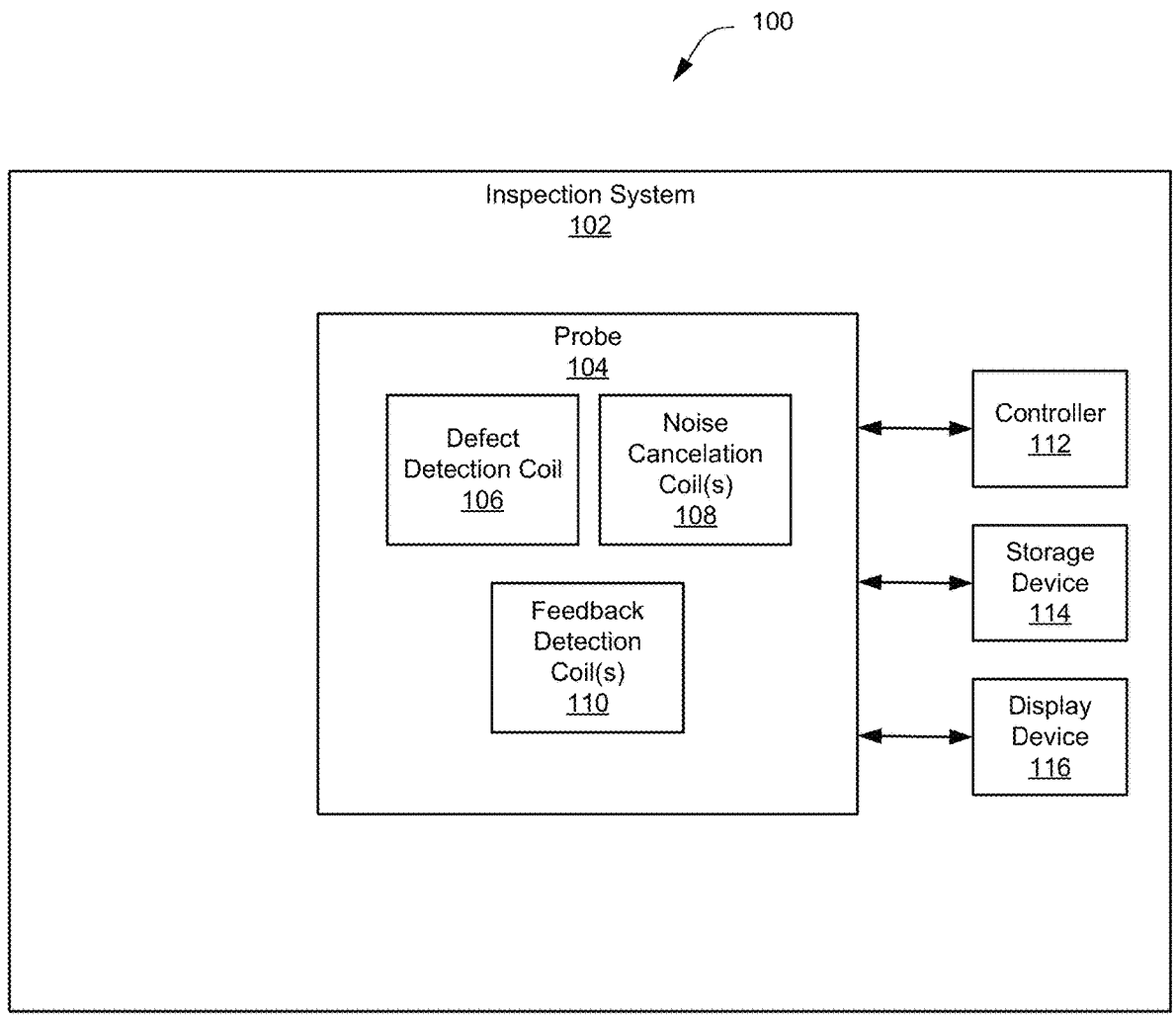
FIG. 1 is a schematic diagram of one embodiment of a system for inspecting a part for defects.

FIG. 1 is a schematic diagram of one embodiment of a system 100 for inspecting a part for defects. The system 100 includes an inspection system 102 for inspecting the part for defects.

Specifically, as illustrated in FIG. 1, the inspection system 102 includes a probe 104 that is locatable in close proximity with a part to inspect the part for defects. To inspect the part for defects, the probe 104 applies an electromagnetic field to the part to produce feedback used to determine whether there are defects in the part.

The probe 104 includes a defect detection coil 106 configured to produce a first electromagnetic field for detecting a defect in the part. Specifically, the defect detection coil 106 includes a coil of conductive wire that is excited with an electrical current (e.g., an alternating electrical current). The defect detection coil 106 produces an alternating magnetic field around itself (e.g., first electromagnetic field). The first electromagnetic field oscillates at the same frequency as the current running through the defect detection coil 106. When the defect detection coil 106 approaches a conductive material, current opposed to the current in the defect detection coil 106 is induced in the material (e.g., eddy current). The presence of certain defects in the part causes a change in eddy current, and a corresponding change in phase and amplitude, that is detectable by measuring the impedance changes in the defect detection coil 106.

The probe 104 also includes one or more noise cancelation coils 108 configured to produce a second electromagnetic field to cancel out at least a portion of the first electromagnetic field. Specifically, the second electromagnetic field overlaps with the first electromagnetic field. In some embodiments, the second electromagnetic field overlaps with the first electromagnetic field and produces an electromagnetic field that is opposite in direction compared to the first electromagnetic field. The portion of the first electromagnetic field that overlaps with the second electromagnetic field produces a low (e.g., or zero) electromagnetic field in the portion. The low electromagnetic field facilitates an increase in the ability of the first electromagnetic field of the probe 104 to detect a defect in a part. For example, a low (e.g., or zero) electromagnetic field means there is low (e.g., or none) eddy current induced in an area, so defects, cracks, and/or edges in an area with the low electromagnetic field may not produce a signal and thus may not inhibit detection of defects in an area of the first electromagnet field. Moreover, the first electromagnetic field is more sensitive to defects under paint and/or less sensitive to a direction of a defect.

The probe 104 includes one or more feedback detection coils 110 configured to detect feedback produced by the first electromagnetic field, the second electromagnetic field, or some combination thereof. The one or more feedback detection coils 110 are used to determine whether the portion of the first electromagnetic field has a low electromagnetic field produced by the second electromagnetic field overlapping with the first electromagnetic field.

The inspection system 102 includes a controller 112 that adjusts settings corresponding to the one or more noise cancelation coils 108 in response to the feedback to reduce electromagnetic noise. In some embodiments, the controller 112 adjusts a voltage and/or current supplied to the one or more noise cancelation coils 108 to adjust the settings corresponding to the one or more noise cancelation coils 108 in order to produce the low electromagnetic field in the portion of the first electromagnetic field.

Furthermore, the inspection system 102 includes a storage device 114 that is configured to store data corresponding to measurements of defects in a part. For example, in certain implementations, the storage device 114 stores measurements of impedance in the defect detection coil 106 to be used to determine whether there are defects in the part.

The inspection system 102 includes a display device 116 used to display data corresponding to measurements of defects in the part. For example, in certain implementations, the display device 116 displays measurements of impedance in the defect detection coil 106 to be used to determine whether there are defects in the part.

Figure 2:
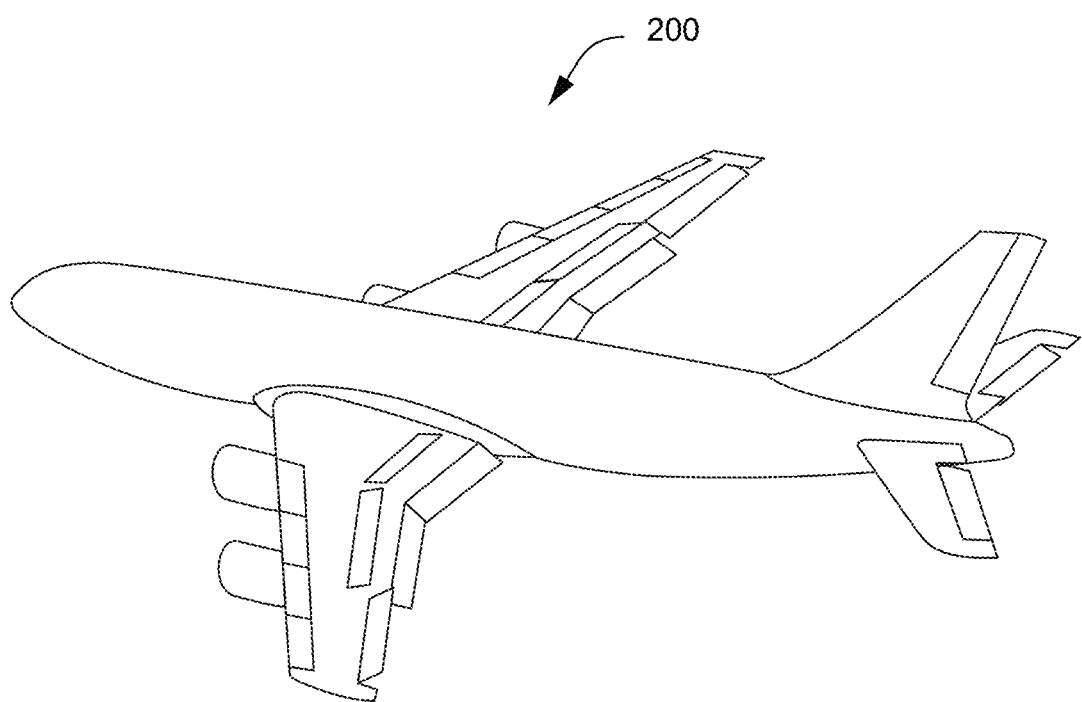
FIG. 2 is a schematic illustration of one embodiment of a system including parts that may be inspected for defects.

FIG. 2 is a schematic illustration of one embodiment of a system 200 including parts that may be inspected for defects using the system 100. As illustrated, aircraft parts may be inspected for defects using the system 100. Moreover, any suitable parts may be inspected for defects using the system 100. For example, aircraft parts, motor vehicle parts, structural parts, satellite parts, space vehicle parts, metallic parts, electronic parts, and so forth may be inspected for defects using the system 100.

Figure 3:
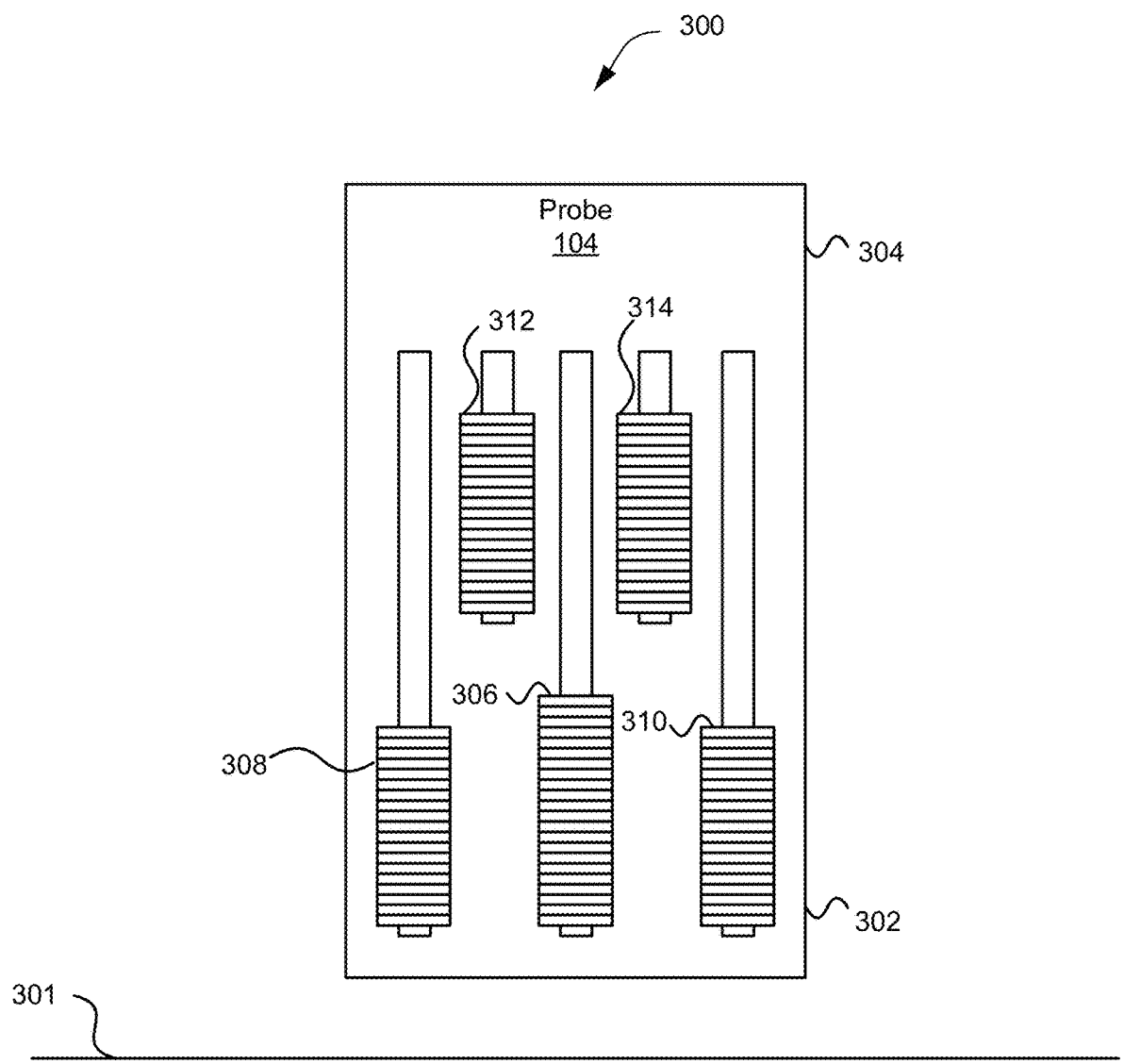
FIG. 3 is a schematic illustration of one embodiment of an apparatus for inspecting a part for defects.

FIG. 3 is a schematic illustration of one embodiment of an apparatus 300 for inspecting a part 301 for defects. The apparatus 300 includes one embodiment of the probe 104 having a first end 302 and a second end 304. The first end 302 is located in close proximity with a part for inspecting the part for defects. The second end 304 may be held by a user for directing the first end 302 toward the part.

The probe 104 includes a defect detection coil 306, a first noise cancelation coil 308, a second noise cancelation coil 310, a first feedback detection coil 312, and a second feedback detection coil 314. As may be appreciated, in some implementations, the defect detection coil 306 is substantially similar to the defect detection coil 106 of FIG. 1, the first 308 and second 310 noise cancelation coils are substantially similar to the one or more noise cancelation coils 108 of FIG. 1, and the first 312 and second 314 feedback detection coils are substantially similar to the one or more feedback detection coils 110 of FIG. 1.

Figure 4:
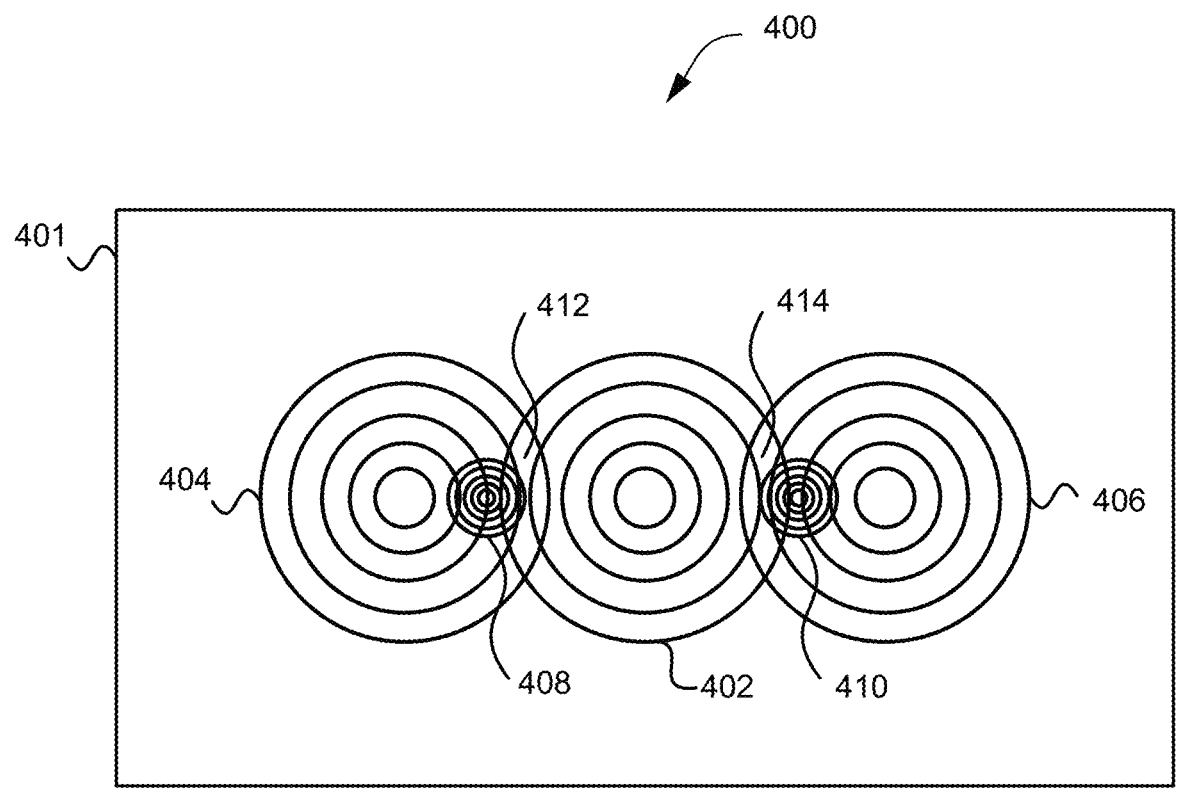
FIG. 4 is a schematic illustration of one embodiment of electromagnetic fields produced for inspecting a part for defects.

FIG. 4 is a schematic illustration of one embodiment of electromagnetic fields 400 produced by the apparatus 300 of FIG. 3 for inspecting a part 401 for defects. Specifically, a first electromagnetic field 402 is produced from the defect detection coil 306, a second electromagnetic field 404 is produced from the first noise cancelation coil 308, a third electromagnetic field 406 is produced from the second noise cancelation coil 310, a fourth electromagnetic field 408 is produced from the first feedback detection coil 312, and a fifth electromagnetic field 410 is produced from the second feedback detection coil 314.

The overlap of the first electromagnetic field 402 and the second electromagnetic field 404 produces a first low (e.g., or zero) electromagnetic field area 412, and the overlap of the first electromagnetic field 402 and the third electromagnetic field 406 produces a second low (e.g., or zero) electromagnetic field area 414. The first 412 and second 414 low electromagnetic field areas enhance the ability of the first electromagnetic field 402 to detect defects in a part.

The fourth 408 and fifth 410 electromagnetic fields illustrate detection fields produced by the first 312 and second 314 feedback detection coils to detect whether the low electromagnetic field areas are being produced by the overlapping first 402, second 404, and third 406 electromagnetic fields. The apparatus 300 uses feedback detected by the first 312 and second 314 feedback detection coils to determine whether settings (e.g., voltage and/or current application) for the first 308 and second 310 noise cancelation coils need to be adjusted to produce the low electromagnetic field areas.

Figure 5:
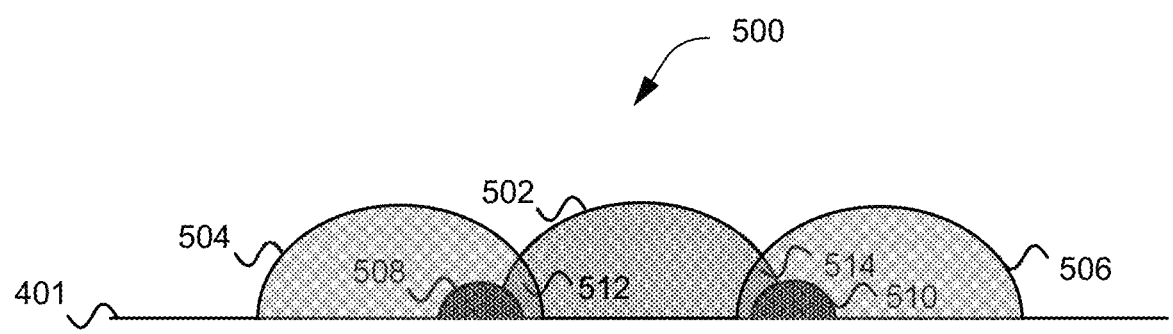
FIG. 5 is a schematic illustration of a different perspective of one embodiment of electromagnetic fields produced for inspecting a part for defects.

FIG. 5 is a schematic illustration of a different perspective of one embodiment of electromagnetic fields 500 produced by the apparatus 300 of FIG. 3 for inspecting a part for defects. Specifically, a first electromagnetic field 502 is produced from the defect detection coil 306, a second electromagnetic field 504 is produced from the first noise cancelation coil 308, a third electromagnetic field 506 is produced from the second noise cancelation coil 310, a fourth electromagnetic field 508 is produced from the first feedback detection coil 312, and a fifth electromagnetic field 510 is produced from the second feedback detection coil 314.

The overlap of the first electromagnetic field 502 and the second electromagnetic field 504 produces a first low (e.g., or zero) electromagnetic field area 512 (e.g., portion), and the overlap of the first electromagnetic field 502 and the third electromagnetic field 506 produces a second low (e.g., or zero) electromagnetic field area 514 (e.g., portion). The first 512 and second 514 low electromagnetic field areas enhance the ability of the first electromagnetic field 502 to detect defects in a part.

The fourth 508 and fifth 510 electromagnetic fields illustrate detection fields produced by the first 312 and second 314 feedback detection coils to detect whether the first 512 and second 514 low electromagnetic field areas are being produced by the overlapping first 502, second 504, and third 506 electromagnetic fields. The apparatus 300 uses feedback detected by the first 312 and second 314 feedback detection coils to determine whether settings (e.g., voltage and/or current application) for the first 308 and second 310 noise cancelation coils need to be adjusted to produce the first 512 and second 514 low electromagnetic field areas.

Figure 6:
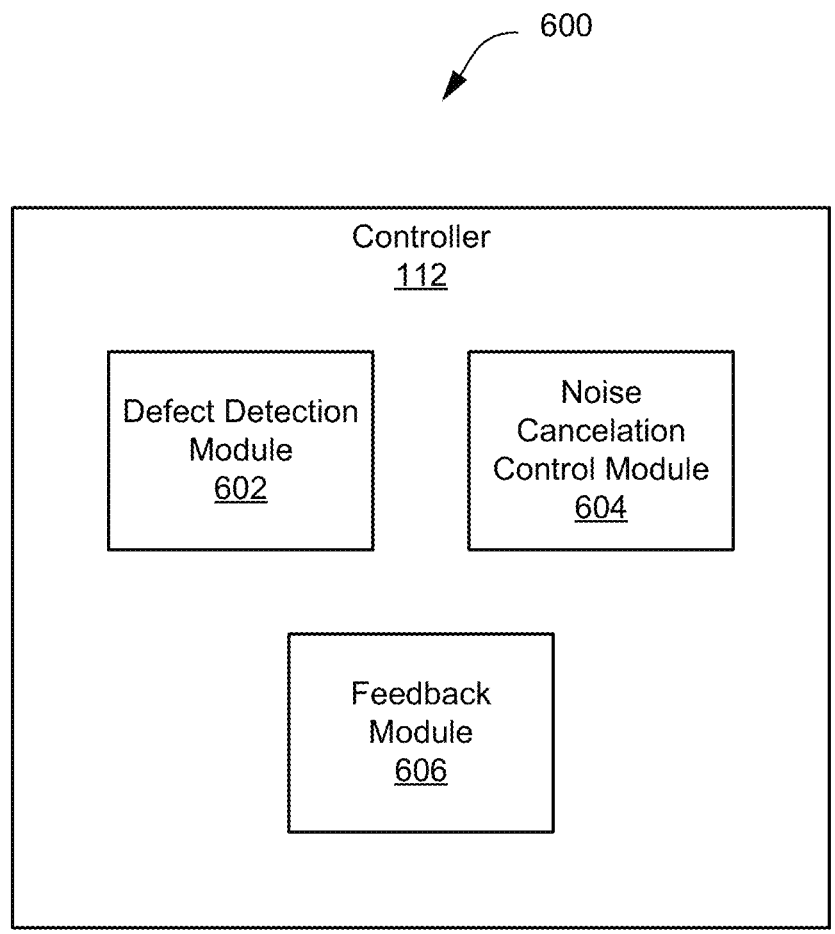
FIG. 6 is a schematic block diagram of one embodiment of a controller for inspecting a part for defects.

FIG. 6 is a schematic block diagram of one embodiment of the controller 112 for inspecting a part for defects. The controller 112 includes a defect detection module 602, a noise cancelation control module 604, and a feedback module 606.

In some embodiments, the defect detection module 602 controls a defect detection coil to produce a first electromagnetic field for detecting a defect in the part. In various embodiments, the defect detection module 602 may control application of a voltage and/or current applied to a defect detection coil (e.g., the defect detection coil 106). In some embodiments, the defect detection module 602 determines whether the part includes a defect based on a measurement corresponding to the first electromagnetic field. For example, in certain embodiments, the defect detection module 602 measures a change in impedance that occurs on the defect detection coil in order to determine whether there is a defect in a part.

In certain embodiments, the noise cancelation control module 604 controls one or more noise cancelation coils (e.g., the one or more noise cancelation coils 108) to produce a second electromagnetic field to cancel out at least a portion of the first electromagnetic field. In one embodiment, the noise cancelation control module 604 controls the one or more noise cancelation coils by controlling a voltage and/or current supplied to the one or more noise cancelation coils. For example, in some embodiments, the noise cancelation control module 604 adjusts settings corresponding to the one or more noise cancelation coils in response to feedback to reduce electromagnetic noise. The feedback may be received from one or more feedback detection coils (e.g., the one or more feedback detection coils 110).

In one embodiment, the feedback module 606 receives feedback produced by the first electromagnetic field, the second electromagnetic field, or some combination thereof. For example, the feedback module 606 receives feedback via one or more feedback detection coils. The feedback module 606 determines whether a low electromagnetic field is produced by an overlap between the first electromagnetic field and the second electromagnetic field. In response to determining whether the low electromagnetic field is produced, the feedback module 606 determines whether the one or more noise cancelation coils need to have settings adjusted and/or directs the noise cancelation control module 604 to adjust such settings.

Figure 7:
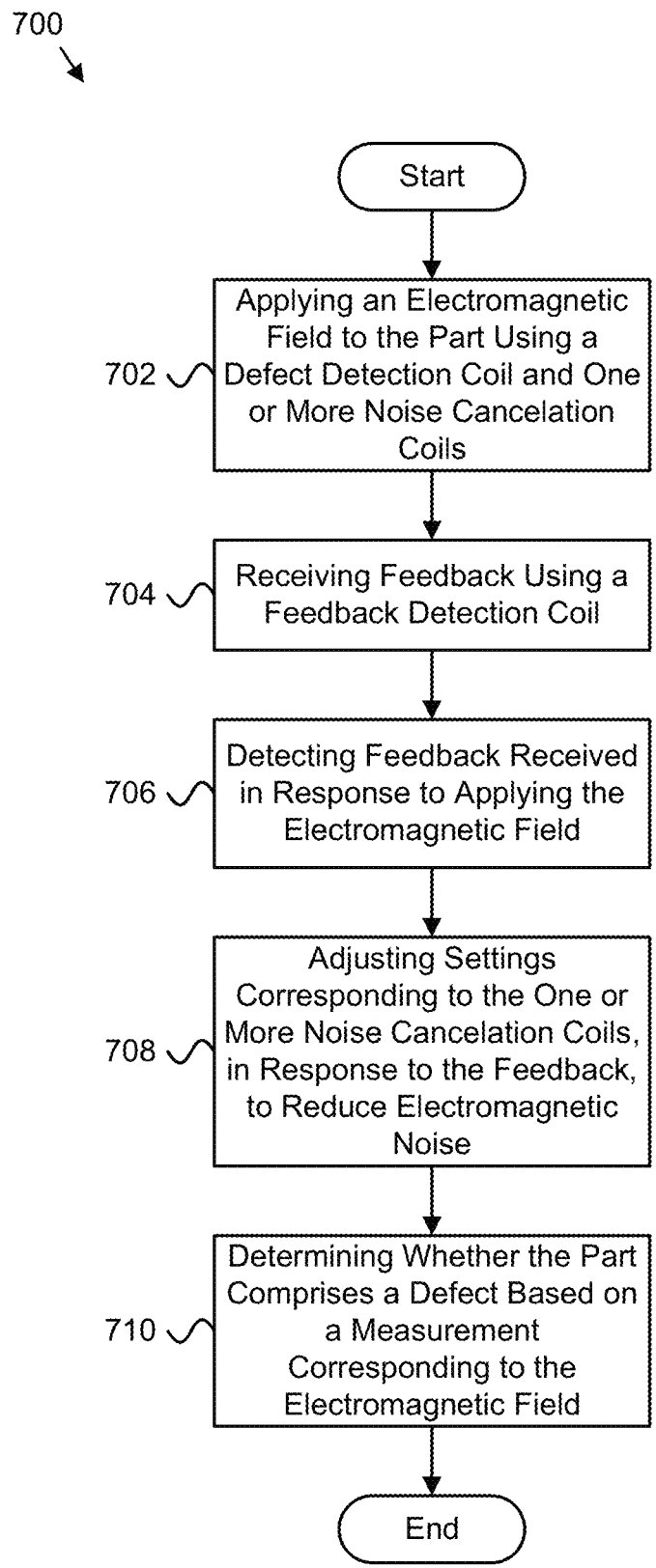
FIG. 7 is a schematic flow diagram of one embodiment of a method for inspecting a part for defects.

FIG. 7 is a schematic flow diagram of one embodiment of a method 700 for inspecting a part for defects according to one embodiment. The method 700 includes applying 702 an electromagnetic field to the part using a defect detection coil (e.g., the defect detection coil 106) and one or more noise cancelation coils (e.g., the one or more noise cancelation coils 108). In some embodiments, applying 702 the electromagnetic field to the part using the defect detection coil and the one or more noise cancelation coils includes applying the electromagnetic field to the part using two noise cancelation coils. In various embodiments, applying 702 the electromagnetic field includes locating a probe in close proximity with the part and activating the probe. The probe includes the defect detection coil and the one or more noise cancelation coils in certain implementations. In one embodiment, the defect detection coil produces a first electromagnetic field and the one or more noise cancelation coils produce a second electromagnetic field. The second electromagnetic field cancels at least a portion of the first electromagnet field to produce a low electromagnetic field at the portion of the first electromagnetic field. The low electromagnetic field may be a zero (or low or near-zero) electromagnetic field.

The method 700 includes receiving 704 feedback using a feedback detection coil (e.g., the one or more feedback detection coils 110). Additionally, the method 700 includes detecting 706 feedback received in response to applying the electromagnetic field.

The method 700 also includes adjusting 708 settings corresponding to the one or more noise cancelation coils, in response to the feedback, to reduce electromagnetic noise. In certain implementations, adjusting 708 settings corresponding to the one or more noise cancelation coils in response to the feedback includes adjusting a voltage supplied to the one or more noise cancelation coils. The method 700 further includes determining 710 whether a part has a defect based on a measurement corresponding to the first electromagnetic field.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Embodiments of the modules of the controller 112 may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

The modules of the controller 112 may be implemented as a hardware circuit comprising custom VLSI circuits or gate arrays, off-the-shelf semiconductors such as logic chips, transistors, or other discrete components. The modules of the controller 112 may also be implemented in programmable hardware devices such as field programmable gate arrays, programmable array logic, programmable logic devices or the like.

The modules of the controller 112 may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized by the modules of the controller 112. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A method of inspecting a part for defects, the method comprising:
    applying an electromagnetic field to the part using a probe comprising a defect detection coil, a feedback detection coil, and one or more noise cancelation coils disposed adjacent to the defect detection coil on the probe, wherein the defect detection coil is configured to detect a defect in the part, the one or more noise cancelation coils are configured to cancel out at least a portion of the electromagnetic field, the feedback detection coil is configured to detect feedback produced by the electromagnetic field, and the defect detection coil is separate from the feedback detection coil;

detecting, by use of the feedback detection coil, feedback received in response to applying the electromagnetic field; and adjusting settings corresponding to the one or more noise cancelation coils, in response to the feedback, to reduce electromagnetic noise.

2. The method of claim 1, further comprising determining whether the part comprises a defect based on a measurement corresponding to the electromagnetic field.

3. The method of claim 1, wherein applying the electromagnetic field to the part using the defect detection coil and the one or more noise cancelation coils further comprises applying the electromagnetic field to the part using two noise cancelation coils.

4. The method of claim 1, wherein:
applying the electromagnetic field comprises locating the probe in close proximity with the part and activating the probe.

5. The method of claim 1, wherein the defect detection coil produces a first electromagnetic field and the one or more noise cancelation coils produce a second electromagnetic field.

6. The method of claim 5, wherein the second electromagnetic field cancels at least a portion of the first electromagnet field to produce a low electromagnetic field at the portion of the first electromagnetic field.

7. The method of claim 6, wherein the low electromagnetic field is a zero electromagnetic field.

8. The method of claim 1, wherein adjusting settings corresponding to the one or more noise cancelation coils in response to the feedback further comprises adjusting a voltage supplied to the one or more noise cancelation coils.

9. An apparatus for inspecting a part for defects, the apparatus comprising:
a probe comprising:
a defect detection coil configured to produce a first electromagnetic field for detecting a defect in the part;
one or more noise cancelation coils configured to produce a second electromagnetic field to cancel out at least a portion of the first electromagnetic field, wherein the one or more noise cancelation coils are disposed adjacent to the defect detection coil on the probe; and
a feedback detection coil configured to detect feedback produced by the first electromagnetic field, the second electromagnetic field, or some combination thereof, wherein settings corresponding to the one or more noise cancelation coils are adjusted in response to the feedback to reduce electromagnetic noise, and the defect detection coil is separate from the feedback detection coil.

10. The apparatus of claim 9, wherein a voltage supplied to the one or more noise cancelation coils is used to adjust the settings corresponding to the one or more noise cancelation coils.

11. The apparatus of claim 9, wherein a measurement corresponding to the first electromagnetic field is used to determine whether the part comprises a defect.

12. The apparatus of claim 9, wherein the one or more noise cancelation coils comprises two noise cancelation coils.

13. The apparatus of claim 9, wherein a low electromagnetic field is produced at the portion of the first electromagnetic field.

14. The apparatus of claim 13, wherein the low electromagnetic field facilitates increasing the ability of the probe to detect a defect in the part.

15. The apparatus of claim 9, wherein the second electromagnetic field blocks external noise from affecting detection of a defect.

16. A controller for controlling inspection of a part for defects, the controller comprising:
a defect detection module that controls a defect detection coil to produce a first electromagnetic field for detecting a defect in the part;
a noise cancelation control module that controls one or more noise cancelation coils to produce a second electromagnetic field to cancel out at least a portion of the first electromagnetic field, wherein a probe comprises the defect detection coil and the one or more noise cancelation coils, and the one or more noise cancelation coils are disposed adjacent to the defect detection coil on the probe; and
a feedback module that receives feedback produced by the first electromagnetic field, the second electromagnetic field, or some combination thereof, wherein the noise cancelation control module adjusts settings corresponding to the one or more noise cancelation coils in response to the feedback to reduce electromagnetic noise, and the defect detection module is separate from the feedback module.

17. The controller of claim 16, wherein the defect detection module determines whether the part comprises a defect based on a measurement corresponding to the first electromagnetic field.

* * * * *